United States Patent
Gogin et al.

(10) Patent No.: US 10,238,361 B2
(45) Date of Patent: Mar. 26, 2019

(54) COMBINATION OF ULTRASOUND AND X-RAY SYSTEMS

(75) Inventors: Nicolas Pierre Bruno Gogin, Paris (FR); Raoul Florent, Ville d'Avray (FR); Pascal Yves Francois Cathier, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1071 days.

(21) Appl. No.: 13/513,921

(22) PCT Filed: Nov. 30, 2010

(86) PCT No.: PCT/IB2010/055494
§ 371 (c)(1),
(2), (4) Date: Jun. 5, 2012

(87) PCT Pub. No.: WO2011/070477
PCT Pub. Date: Jun. 16, 2011

(65) Prior Publication Data
US 2012/0245458 A1 Sep. 27, 2012

(30) Foreign Application Priority Data
Dec. 9, 2009 (EP) .................................. 09306203

(51) Int. Cl.
*A61B 6/12* (2006.01)
*A61B 8/00* (2006.01)
(Continued)

(52) U.S. Cl.
CPC .................. *A61B 8/00* (2013.01); *A61B 6/00* (2013.01); *A61B 6/12* (2013.01); *A61B 6/5247* (2013.01); *A61B 8/4245* (2013.01); *A61B 8/4416* (2013.01); *A61B 6/503* (2013.01); *A61B 8/0883* (2013.01)

(58) Field of Classification Search
CPC .. A61B 6/00; A61B 6/12; A61B 6/503; A61B 6/5247; A61B 8/00; A61B 8/0883; A61B 8/4245; A61B 8/4416
See application file for complete search history.

(56) References Cited

U.S. PATENT DOCUMENTS

| 5,207,225 A | 5/1993 | Oaks et al. |
| 6,996,430 B1 | 2/2006 | Gilboa et al. |

(Continued)

FOREIGN PATENT DOCUMENTS

WO WO2008062358 5/2008

OTHER PUBLICATIONS

Ma et al., "Evaluation of a Robotic Arm for Echocardiography to X-Ray Image Registration During Cardiac Catheterization Procedures", 31st Annual International Conference of the IEEE EMBS, Minneapolis, MN, US, Sep. 2-6, 2009, pp. 5829-5832.
(Continued)

*Primary Examiner* — Mark Remaly

(57) ABSTRACT

The invention proposes to detect and track an intervention device in a 2D fluoroscopy image and to steer an ultrasound probe beam towards this device. Therefore, a method and corresponding system is proposed, by which an ultrasound probe is registered in a fluoroscopy image, wherein the registering includes the estimation of the position and of the orientation of the probe relative to the fluoroscopy.

17 Claims, 4 Drawing Sheets

(51) Int. Cl.
 *A61B 6/00* (2006.01)
 *A61B 8/08* (2006.01)

(56) References Cited

U.S. PATENT DOCUMENTS

| | | |
|---|---|---|
| 2005/0261591 A1* | 11/2005 | Boctor et al. ............... 600/462 |
| 2006/0036162 A1* | 2/2006 | Shahidi ................ A61B 5/06 |
| | | 600/424 |
| 2006/0241417 A1 | 10/2006 | Edwardsen |
| 2006/0241465 A1* | 10/2006 | Huennekens .......... A61B 6/504 |
| | | 600/458 |
| 2006/0247520 A1 | 11/2006 | McGee |
| 2007/0276243 A1 | 11/2007 | Gerard et al. |
| 2008/0146919 A1 | 6/2008 | Camus et al. |
| 2008/0146942 A1 | 6/2008 | Dala-Krishna |
| 2009/0088628 A1 | 4/2009 | Klingenbeck-Regn |
| 2009/0185657 A1 | 7/2009 | Klingenbeck-Regn |

OTHER PUBLICATIONS

French, et al., "Computing Intraoperative Dosimetry for Prostate Brachytherapy Using TRUS and Fluoroscopy", University of British Columbia, Electrical and Computer Engineering, Vancouver BC, Canada, Jan. 16, 2005, pp. 1262-1272.

* cited by examiner

COMBINATION OF ULTRASOUND AND X-RAY SYSTEMS

FIELD OF THE INVENTION

The present invention relates to x-ray guided procedures. Especially, the invention relates to a method for processing an x-ray image. Furthermore, the invention relates to a system comprising an x-ray system as well as an ultrasound system, wherein the system is equipped with a computer program for performing the method.

BACKGROUND OF THE INVENTION

One of the challenges of image-guided medical and surgical procedures is to efficiently use the information provided by the many imaging techniques the patient may have been through before and during the intervention.

In cardiology, for example the physician often has access to real-time x-ray images acquired by a C-arm. These images have a very good spatial and temporal accuracy enable to follow precisely the progression of thin catheters and other interventional tools. However, soft-tissues are barely visible in these images, and furthermore, these images are projections which do not give a direct access to the volumetric geometry of the intervention scene. To gain access to this important information, a solution consists in using a second imaging modality which is both 3D and able to image soft-tissues.

One possible choice for this second imaging system is 3D ultrasound imaging. The advantage of this modality is that it can be used in real-time during the surgical procedure. In cardiological procedure, trans-esophageal probes can be navigated right next to the heart, producing real-time volumetric images with anatomical details that are hardly visible with standard transthoracic ultrasound.

Typical interventions currently involving this modality combination are ablation for atrial fibrillation, PFO closure (or other septal default repair), and percutaneous valve repair (PVR). All those interventions are x-ray centric, but in all of them, the simultaneous involvement of ultrasound is either very helpful or completely mandatory to monitor the placement of the tool/endoprosthesis with respect to the soft-tissue anatomy.

Although the ultrasound probe can deliver very useful images of the anatomy, an important drawback is the compromise that exists between the temporal acquisition frame rate and the extent of the field of view. It is therefore necessary to have a small field of view to acquire images at high frame rate.

But it is often difficult to select the optimum field of view, which size is constraint by the acquisition frame rate but which at the same time should include the area to be visualized.

Generally, a volume with a large field of view is first acquired and is used to select small sub-regions within this first acquisition corresponding to the area of interest. In many interventions, the area of interest would include the interventional tools or some of them. So in practice, the acquisition volume could be targeted around the interventional tools. Unfortunately, the interventional tools cannot be easily visualized in ultrasound due to artifacts (acoustic reflections, shadows, etc.) and limited spatial resolution.

As a consequence, the actual steering of the probe beam so that it encompasses the interventional instrument is uneasy and requires specialized skill and attention. And this is made worse in interventions where both the anatomy and the device undergo strong movements (atrial fibrillation ablation, PFO closure, PVR).

Ultrasound through x-ray registration is usually performed using image-based registration techniques aiming at lining common structures visualized by both modalities. This approach has several drawbacks.

An important one is the difficulty to include the registration landmarks in the field of view which can be very limited in trans-esophageal echocardiograms (TEE). Moreover, natural landmarks such as the heart contours cannot be used because they are not visible in x-ray. The use of interventional tools as registration landmarks is challenging as they are not well defined in the ultrasound volume due to noise and artifacts.

Ultrasound to x-ray registration can also be achieved using tracking systems which give the position of the ultrasound probe with respect to the x-ray imaging system. Unfortunately, the ultrasound probe does not come with a standard tracking system that could be attached to the x-ray imaging system. Many systems have been designed to gap that void using physical trackers such as magnetic devices. These systems may be expensive and have several disadvantages: they can be disrupted by interference and require additional calibration steps which are prone to error.

SUMMARY OF THE INVENTION

It is an object of the invention to provide a system and method for a combination of ultrasound and x-ray images.

It is a further object of the invention to provide a system and method for detecting the position and orientation of an ultrasound probe in an x-ray image.

It is a further object of the invention to provide a system and method for a better visualization of both an ultrasound and an x-ray image.

This is achieved by the subject matter of the respective independent claims. Further embodiments are described in the respective dependent claims.

In general, this is achieved by a method for a combination of ultrasound and x-ray images, comprising the steps of receiving an x-ray image, detecting an ultrasound probe in the x-ray image, and registering the probe including an estimation of a position and an orientation of the probe relative to a reference coordinate system.

It is noted that the reference coordinate system may be any pre-determined coordinate system. For example, the reference coordinate system may be within the plane of the x-ray image or may be defined relative to the C-arm of an x-ray system which may be used while performing the method.

According to another embodiment of the invention, the method comprises further a step of matching a digitally rendered projection of a 3D model of the probe with the detected probe in the x-ray image, wherein the estimation of the position and orientation of the probe is retrieved from the 3D model of the probe.

According to another aspect of that embodiment, the 3D model is retrieved from a CT acquisition or is a computer-aided design model.

Accordingly, a 2D x-ray image of an ultrasound probe may be registered with a 3D model of the probe which can be either a 3D acquisition of the probe or a computer-aided design (CAD). This registration is performed by matching a digitally rendered radiograph of the probe and the real x-ray projection of the probe. It is noted that a graphic processing unit (GPU) based algorithm may be used to generate digitally rendered radiograph in an efficient way.

The 2D-3D registration of the ultrasound probe gives the 3D pose of the probe with respect to the x-ray imaging system. There are several interesting applications such as merging the ultrasound image with x-ray image or ultrasound volume compounding in order to build an extended field of view.

The method may further comprise a step of visualizing an acquisition setting of the probe in the x-ray image. By way of this, the operator can easily adjust the acquisition settings thanks to the information visualized in x-ray. It provides an interactive way to change the acquisition settings of the ultrasound acquisition system during an interventional procedure.

The acquisition setting may be the field of view of an ultrasound probe. The volume of the field of view of the ultrasound probe can be represented as a truncated pyramid in 3D. This pyramid may be indicated by the outlines of an area which can be visualized by an ultrasound system. Further, the pyramid may be defined by its centre together with parameters like the distance to the ultrasound sensor of the probe, a width, length, angle and/or a depth of the pyramid. The volume of the field of view may also be a truncated pyramid in one plane having a constant thickness perpendicular to said plane. With an appropriate calibration, the truncated pyramid can be projected and displayed in the x-ray image. As the operator changes the acquisition of the probe, the display of the acquisition volume in the x-ray image is automatically updated to provide a direct feedback to the operator.

Alternatively, one or more parameter like a main direction, an angle, a distance, a frame rate or a coordinate system, may be visualized in the x-ray image. The visualization of such parameters may be provided by for example points or lines or by numerals at an appropriate position in the x-ray image. A main direction may be a direction perpendicular to the surface of the ultrasound sensor or sensors at the ultrasound probe. A distance may be the distance of the ultrasound sensor to the center of the field of view or to a center of a reference coordinate system or to an interventional device also visible in the x-ray image or to any other predetermined point in the x-ray image.

This may allow for an interactive adjustment of the acquisition settings of the ultrasound acquisition system, through direct visualization in an x-ray acquisition system. By way of this, it may be easier for a clinician to adjust the orientation of an ultrasound probe relative to an interventional device like a catheter, wherein this catheter may be located within the truncated pyramid, i.e. within the field of view of the ultrasound probe.

According to another aspect of the invention, the method further comprises the step of detecting an interventional device in the x-ray image and manipulating the probe so that the interventional device is within the field of view of the probe. It is noted that this manipulation may be performed manually as well as automatically.

Accordingly, it may be possible to detect and track an interventional device in 2D x-ray image and to steer an ultrasound probe beam towards this device. The field of view of a probe can be automatically steered, and additionally the appearance of the intervention device in the fluoroscopy may be modified by for example blinking, flashing or coloring, when the device or at least a part of the device enters or is present in the field of view of the ultrasound probe. By way of this, the visualization will be enhanced and will dramatically help the steering of the ultrasound probe beam in the interventional context.

Finally, the method may further comprise the step of overlaying an ultrasound image provided by the probe over the x-ray image. Furthermore, it may be possible to overlay a plurality of ultrasound images over only one x-ray image. This may provide for an extended field of view.

It is noted that the interventional device may be a flexible or stiff catheter or a biopsy device, a canula or trokar. The ultrasound probe may also be a trans-esophageal echocardiography ultrasound probe.

According to another aspect of the invention, a computer program is provided by means of which the above described method may be performed automatically, or at least predominantly automatically. Therefore, the computer program comprises sets of instructions for storing a x-ray image generated by an x-ray system, sets of instructions for detecting an ultrasound probe in that x-ray image, and sets of instructions for registering the probe and thus estimating the position and orientation of the ultrasound probe relative to a reference coordinate system. Furthermore, the computer program may comprise sets of instructions for receiving data representing a 3D model of the ultrasound probe.

Such a computer program may be implemented according to a further embodiment of the invention in a system including an x-ray system, an ultrasound system with a ultrasound probe, and a processing unit. Usually, such a system will include also a monitor for a visualization of the ultrasound as well as the x-ray images.

Such a computer program is preferably loaded into a work memory of a data processor. The data processor is thus equipped to carry out the method of the invention. Further, the invention relates to a computer readable medium, such as a CD-ROM, at which the computer program may be stored. However, the computer program may also be presented over a network like the World Wide Web and can be downloaded into the work memory of the data processor from such a network.

It will be understood that such a computer program may be either provided as software as well as maybe implemented (at least partially) as hardware of a processing unit.

It has to be noted that the embodiments of the invention are described with reference to different subject matters. In particular, some embodiments are described with reference to method type claims whereas other embodiments are described with reference to apparatus type claims. However, a person skilled in the art will gather from the above and the following description that, unless or other notified, in addition to any combination of features belonging to one type of subject matter also any combination between features relating to different subject matters is considered to be disclosed with this application.

The aspects defined above and further aspects, features and advantages of the present invention can also be derived from the examples of the embodiments to be described hereinafter and are explained with reference to examples of embodiments also shown in the figures but to which the invention is not limited.

DETAILED DESCRIPTION OF THE EMBODIMENTS

Figure 1:
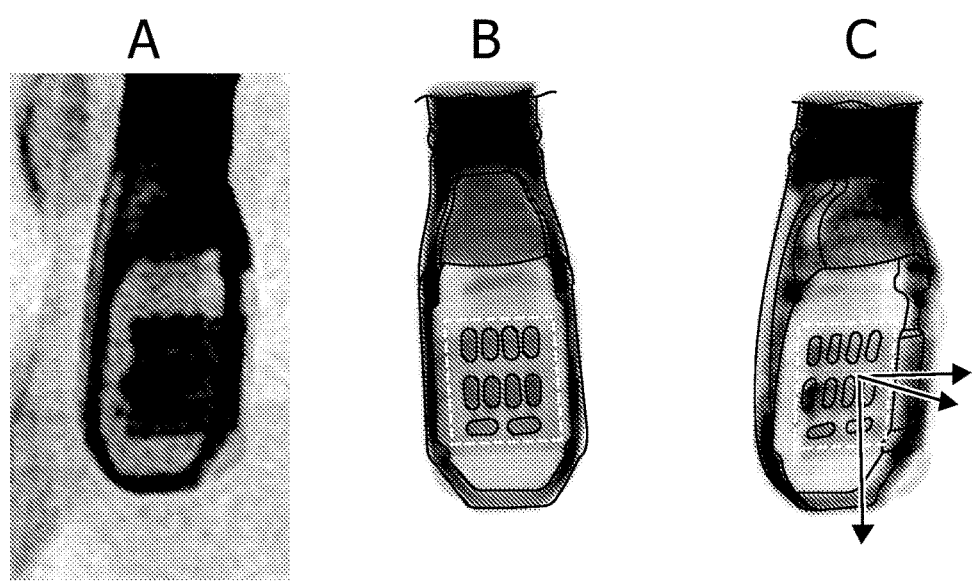
FIG. 1a shows an ultrasound probe retrieved from a CT acquisition.
FIG. 1b shows a non-aligned 3D model.
FIG. 1c shows an aligned 3D model.

FIG. 1 shows, from left to right, an x-ray target image of an ultrasound probe, a non-aligned digitally rendered radiograph (DRR) of an ultrasound probe, as well as an aligned DRR. In FIG. 1c, the 3D model of FIG. 1b is orientated so that a projection thereof matches with the projection of the probe in the x-ray image of FIG. 1a.

Figure 2:
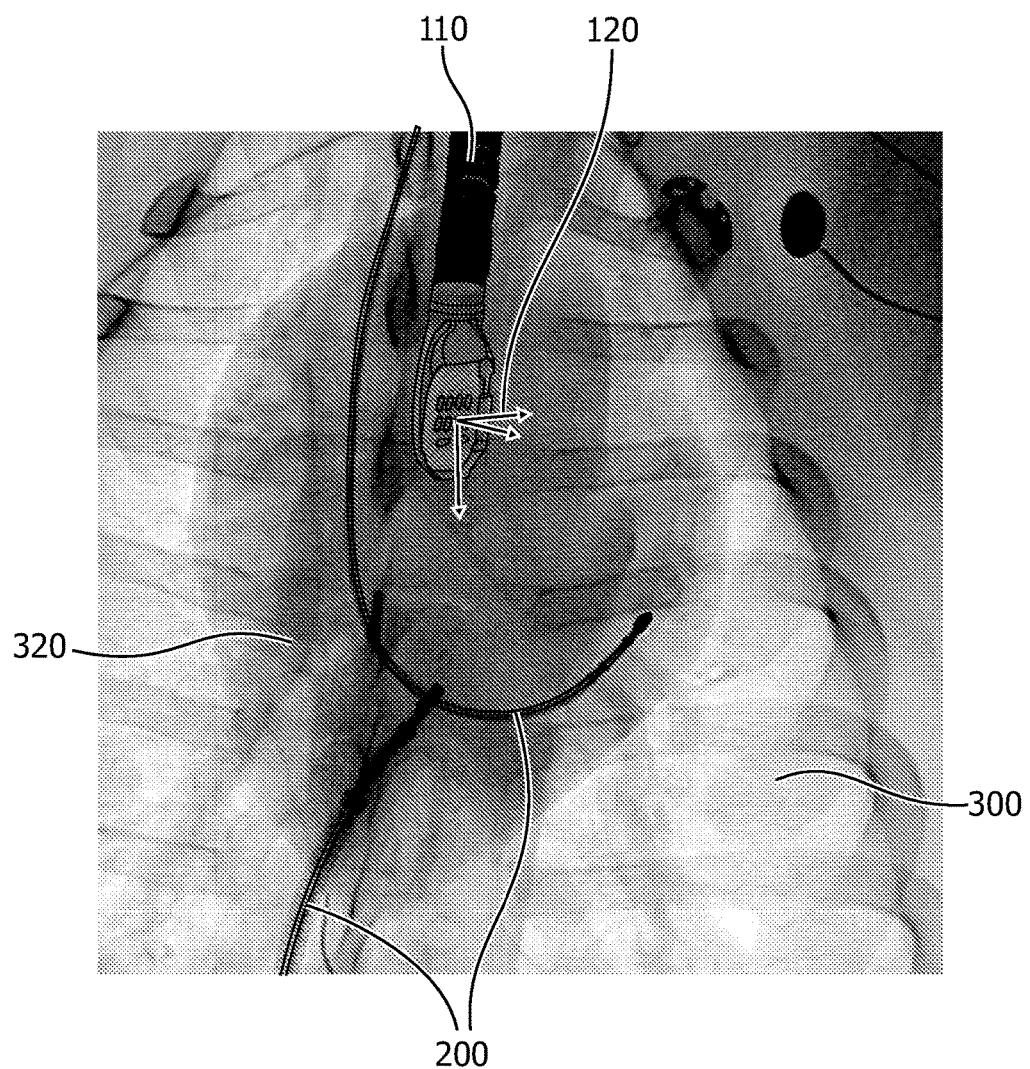
FIG. 2 shows an x-ray image including an ultrasound probe.

The orientated 3D model of FIG. 1c is then combined with the x-ray image. FIG. 2 shows such an overlay of an aligned DRR 110 on top of an x-ray image of chest 300 and heart 320, after intensity based registration, i.e. an estimation of the position and orientation of the probe. This gives the position/orientation of the probe with respect to the x-ray imaging system. If both systems are calibrated, the ultrasound image can be merged with the x-ray image. Also shown in FIG. 2 are interventional devices 200, for example catheters. A coordinate system in front of the ultrasound probe 110 indicates the estimated orientation of the ultrasound sensor elements relative to the image plane of the x-ray image.

An x-ray acquisition system is configured to produce real-time 2D x-ray images of an anatomical region during an interventional procedure. This modality does not allow clear visualization of complex soft-tissue anatomy such as the heart.

An ultrasound acquisition system with for example a trans-esophageal echocardiography (TEE) ultrasound probe, is configured to produce images of the anatomy. This ultrasound acquisition system is assumed to lie at least partially in the field of view of the x-ray acquisition system with sufficient information that it is enough to recover the coordinate system of the images produced by this system. It is the case for example when the whole detector of the ultrasound acquisition system is present in the x-ray image and/or when its position can be estimated from other structures present in the x-ray image.

Subsequently, a 3D model of the ultrasound probe may be used to automatically compute the pose of the probe. This may be done by matching the x-ray image of the ultrasound probe with a digitally rendered radiograph generated by transparent projection of the 3D model (cf. FIGS. 1 and 2). An optimization algorithm allows retrieving the 6 pose-parameters of the probe which gives the 3D position of the probe and its 3D orientation with respect to for example the C-arm system defining a reference coordinate system.

An offline calibration of the probe gives the relationship between the ultrasound image and the 3D model. In combination with the previous step, it is then possible to have the relationship between the ultrasound image and the x-ray imaging system, and therefore with the x-ray image if the x-ray imaging system is also calibrated.

Fusion between x-ray image and ultrasound image is then straight forward. Another interesting application is the use of the x-ray imaging system as a reference coordinate system to compound different ultrasound acquisition and build an extended field of view which is of great interest for TEE acquisitions where the field of view is often very limited.

Figure 3:
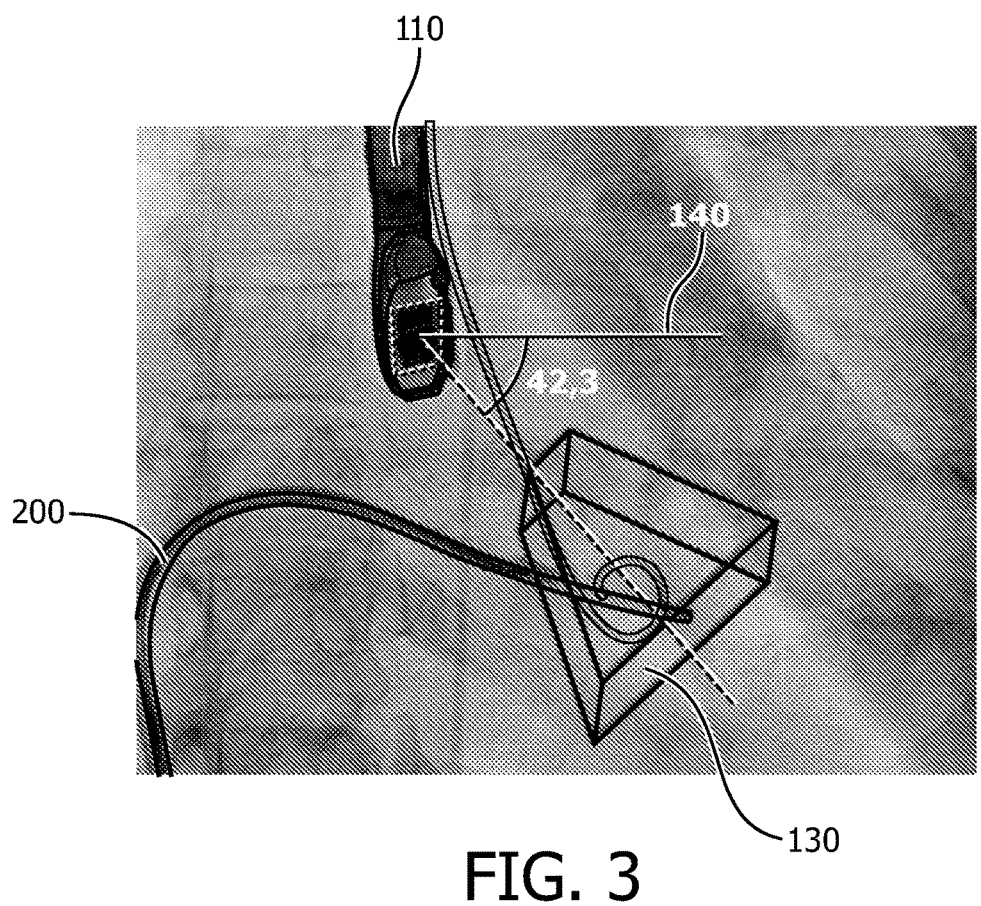
FIG. 3 shows an x-ray image including an ultrasound probe as well as a schematic visualization of the field of view of said probe.

As exemplarily shown in FIG. 3, the volume of acquisition 130 of the ultrasound probe 110 may be represented as a truncated pyramid in 3D, assuming that the position and orientation of the ultrasound probe 110 with respect to the x-ray image is known. As can be seen in FIG. 3, an interventional device 200 with its interventional end portion may be located such that the field of view 130 encompasses that interventional end portion of the device 200. Further shown in FIG. 3 is an angle 140 determining the angle of beam of the field of view of the ultrasound probe. Here, the angle of beam is 42.3 degree.

Figure 4:
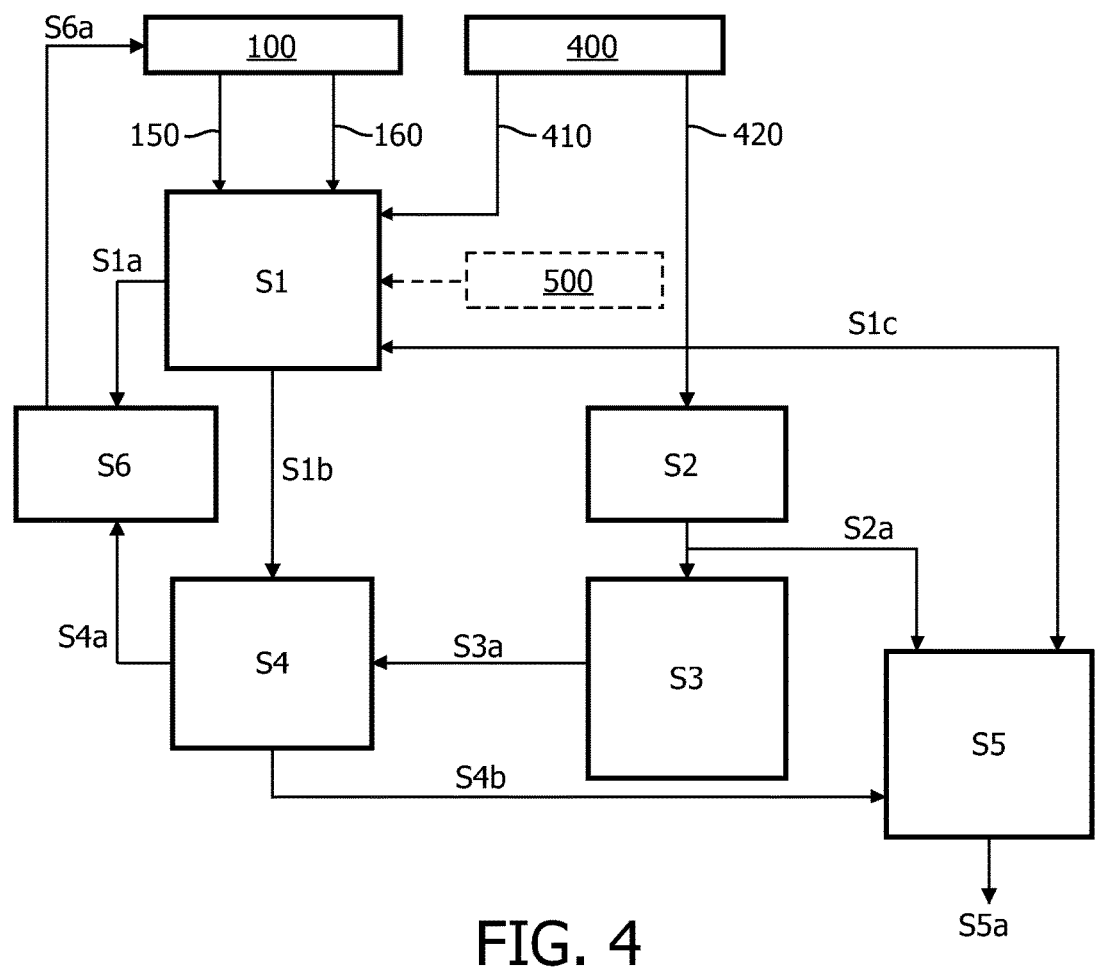
FIG. 4 is a diagram illustrating the system and method according to the invention.

In FIG. 4 is a flow chart showing the steps of a method for a combination of ultrasound and x-ray images according to the invention. The patient is simultaneous imaged by an ultrasound system 100 and an x-ray system 400. In a preferred embodiment, a considered ultrasound probe of the ultrasound system 100 is capable of generating synthetically steered beams, preferably in 3D.

It will be understood that the steps described with respect to the method are major steps, wherein these steps might be differentiated or divided into several sub-steps. Furthermore, there might be also sub-steps between these major steps. Therefore, a sub-step is only mentioned if that step is important for the understanding of the principles of the method according to the invention.

In step S1, the ultrasound system 100 and the x-ray imaging system 400 are first mutually registered. This can typically be achieved by imaging the probe of the ultrasound system 100 by the x-ray system 400, and based on the settings 150 and data 160 of the ultrasound system 100 and on the settings 410 of the x-ray system 100, plus on the possible use of a probe 3D model 500 or markers, in determining the position of the probe in the x-ray referential. From this information, and based on the relevant calibration information, one can use the parameters of the probe field of view in the x-ray referential, as described above. Data S1c will be exchanged for visualization of the resulting image.

In step S2, at the same time, the intervention device (for instant the tip of a catheter), is detected and tracked in the x-ray images. This step relies on data 420 of the x-ray system 400 and on usual object detection means that rely on the spatial signature of the device and possibly on its motion characteristics (for instance, the device is animated by a cardiac motion plus a steering motion, seen in projection).

In step S3, it is advantageous to improve the 2D location provided by device tracking in the x-ray images and to try to get a depth estimation of the considered device. Several approaches are possible to reach the goal, among which the exploitation of the devices observed width, the use of other x-ray views under different angulation for instance in bi-plane context or the use of wiggling motions. For example, the width of the ultrasound probe may be estimated, wherein subsequently possible locations of the ultrasound probe are discriminated on the basis of the estimated size and of a segmentation of the imaged object.

In step S4, the device-improved location S3a can then be compared to the found ultrasound field of view S1b, and several commands can be issued accordingly. For instance, a device flashing/blinking command can be issued to the imaging processing channel of the x-ray data stream, or a probe steering command S4a can be sent to the relevant module.

On the other hand, the data S4b of step S4 together with the information S2a of step S2 will result in step S5, i.e. the visualization of the device in the x-ray image which is adapted based on events such as the entering (blinking/flashing) or the presence (coloring) of the device in the ultrasound field of view. This provides the ultrasound user with an easy way of controlling the steering of the probe based on the high resolution x-ray images. Of course, this steering is also made easier by the visualization of the ultrasound cone as shown in FIG. 3. The result of step S5 is an enhanced 2D view S5a facilitating the steering of the ultrasound probe.

In step S6, alternatively or complementarily, a command S6a can be issued to the beam-steering module of the ultrasound system 100, as to which field of view one should generate in order to nicely visualize the device at the center of the ultrasound cone (volume or image). The probe steering module, based on the ultrasound/x-ray registration information will determine and apply the relevant set parameters enabling this device-driven steering.

When the invention has been illustrated and described in detail in the drawings and afore-going description, such illustrations and descriptions are considered illustrative or exemplary and not restrictive, the invention is not limited to the disclosed embodiments.

Other variations to the disclosed embodiments can be understood and effected by those skilled in the art in practicing the claimed invention, from a study of the drawings, the disclosure and the pendent claims. In the claims, the word comprising does not exclude other elements or steps, and the indefinite article a or an does not exclude a plurality. A single processor or other unit may fulfill the functions of several items recited in the claims. The mere effect that certain measures are recited and mutually different, dependent claims does not indicate that a combination of these measured cannot be used to advantage. A computer program may be stored/distributed on a suitable medium such as an optical storage medium or a solid-state medium supplied together with or as a part of another hardware, but may also be distributed in other forms, such as via the internet or other wired or wireless telecommunication systems. Any reference signs in the claims should not be construed as limiting the scope.

LIST OF REFERENCE SIGNS 100 ultrasound system
110 ultrasound probe
120 ultrasound probe coordinate system
130 field of view
140 angle of field of view
150 ultrasound probe settings
160 ultrasound data stream
200 interventional device
300 chest
320 heart
400 x-ray system
410 x-ray acquisition parameters
420 x-ray data stream
500 3D probe model
S1a registration parameter
S1b ultrasound field of view in x-ray referential
S1c data exchange
S2a device localization
S3a improved device localization
S4a probe steering commands
S4b in field of view signal
S5a enhanced 2D view of manual steering
S6a probe parameter

The invention claimed is:

1. An apparatus comprising:
an x-ray acquisition system configured to produce an x-ray image of an anatomical region in an x-ray field of view;
an ultrasound probe configured to image at least a portion of the anatomical region, wherein the ultrasound probe is at least partially positionable in the x-ray field of view to generate a target image of the ultrasound probe in the x-ray image; and
a processing unit configured to:
acquire x-ray image data including the target image of the ultrasound probe from the x-ray image;
detect the ultrasound probe in the x-ray image data;
register the ultrasound probe relative to a reference coordinate system by matching a digitally rendered projection of a three-dimensional model of the ultrasound probe with the target image to provide an estimated position and orientation of the ultrasound probe;
combine the digitally rendered radiograph projection and the x-ray image data including the target image to form an aligned composite image; and
display the aligned composite image.

2. The apparatus of claim 1, wherein the processing unit is further configured to retrieve the three-dimensional model from either a CT acquisition or a computer-aided design model.

3. The apparatus of claim 1, wherein the processing unit is further configured to register the ultrasound probe in response to detection of the ultrasound probe in the x-ray image data.

4. The apparatus of claim 1, wherein the x-ray acquisition system comprises a C-arm configured to produce the x-ray image, wherein the reference coordinate system is defined relative to the C-arm.

5. A non-transitory computer readable medium comprising a computer program having a set of instructions for reading data from a processor in an apparatus which is in communication with an x-ray acquisition system, the instructions when executed on the processor configure the apparatus to:
acquire x-ray image data including the target image of the ultrasound probe from the x-ray image;
detect the ultrasound probe in the x-ray image data;
register the ultrasound probe relative to a reference coordinate system by matching a digitally rendered projection of a three-dimensional model of the ultrasound probe with the target image to provide an estimated position and orientation of the ultrasound probe;
generate a field of view volume of the ultrasound probe that is aligned with the estimated position and orientation;
combine the field of view volume and the x-ray image data including the target image to form an aligned composite image;
display the aligned composite image; and
update the field of view volume for maintaining an interventional device within the field of view volume as the interventional device moves.

6. The computer readable medium of claim 5, wherein the instructions when executed on the processor further configure the apparatus to:
determine whether the interventional device is at least partially within the field of view volume; and
highlight a visualization of the interventional device in the aligned composite image when the interventional device is determined to be at least partially in the field of view.

7. The computer readable medium of claim 5, wherein the instructions when executed on the processor further configure the apparatus to provide a real time update for maintaining the interventional device within the field of view.

8. An apparatus comprising:
an x-ray acquisition system configured to produce an x-ray image of an anatomical region in an x-ray field of view;
an ultrasound probe configured to image at least a portion of the anatomical region, wherein the ultrasound probe is at least partially positionable in the x-ray field of view to generate a target image of the ultrasound probe in the x-ray image; and
a processing unit having a data processor executing instruction in a computer program stored in a work memory of the data processor and configured to:
acquire x-ray image data including the target image of the ultrasound probe from the x-ray image;
detect the ultrasound probe in the x-ray image data;
register the ultrasound probe relative to a reference coordinate system by matching a digitally rendered projection of a three-dimensional model of the ultrasound probe with the target image to provide an estimated position and orientation of the ultrasound probe;
generate a field of view volume of the ultrasound probe that is aligned with the estimated position and orientation; and
determine whether an interventional device is within the field of view volume based on registering the ultrasound probe and at least one parameter of the ultrasound probe.

9. The apparatus of claim 8, wherein the processing unit is further configured to:
combine the field of view volume and the x-ray image data including the target image to form an aligned composite image; and
display the aligned composite image tracking the ultrasound probe in real time.

10. The apparatus of claim 8, wherein the processing unit is further configured to acquire ultrasound image data from the ultrasound probe, and display the x-ray image data overlaid on the ultrasound image data.

11. The apparatus of claim 8, wherein the processing unit is further configured to:
determine a location of the interventional device from the x-ray image data;
estimate a depth of the interventional device relative to the x-ray image data; and
determine whether the interventional device is within the field of view volume based on the estimated depth.

12. The apparatus of claim 8, wherein the processing unit is further configured to determine in real time whether the interventional device is within the field of view volume in response to detect the ultrasound probe in the x-ray image data.

13. The apparatus of claim 8, wherein the processing unit is further configured to register the ultrasound probe based on settings of the ultrasound system, settings of the x-ray acquisition system, and the x-ray image data.

14. An apparatus comprising:
an x-ray acquisition system configured to produce an x-ray image of an anatomical region in an x-ray field of view;
an ultrasound probe configured to image at least a portion of the anatomical region, wherein the ultrasound probe is at least partially positionable in the x-ray field of view to generate a target image of the ultrasound probe in the x-ray image; and
a processing unit configured to:
acquire x-ray image data including the target image of the ultrasound probe from the x-ray image;
detect the ultrasound probe in the x-ray image data;
register the ultrasound probe relative to a reference coordinate system by matching a digitally rendered projection of a three-dimensional model of the ultrasound probe with the target image to provide an estimated position and orientation of the ultrasound probe;
generate a field of view volume of the ultrasound probe that is aligned with the estimated position and orientation;
track an interventional device in the x-ray image data; and
generate synthetically steered ultrasound beams with the ultrasound probe by comparing the tracked interventional device to the field of view volume for maintaining the interventional device within the field of view volume.

15. The apparatus of claim 14, wherein the processing unit is further configured to register the ultrasound probe without landmark detection.

16. The apparatus of claim 14, wherein the processing unit is further configured to mutually register the ultrasound system with the x-ray acquisition system.

17. The apparatus of claim 16, wherein the processing unit is further configured to determine a position of the ultrasound probe in an x-ray referential for mutually registering the ultrasound system with the x-ray acquisition system.

* * * * *